United States Patent [19]

Marini et al.

[11] Patent Number: 4,605,924
[45] Date of Patent: Aug. 12, 1986

[54] METHOD AND APPARATUS FOR ACOUSTICALLY MONITORING AN INDUSTRIAL PLANT

[75] Inventors: Jean Marini, Marly le Roi; Bernard Audenard, Orgeval, both of France

[73] Assignee: Framatome & CIE, Courbevoie, France

[21] Appl. No.: 575,491

[22] Filed: Feb. 1, 1984

Related U.S. Application Data

[63] Continuation-in-part of Ser. No. 301,848, Sep. 14, 1981, abandoned.

[30] Foreign Application Priority Data

Oct. 2, 1980 [FR] France ............................ 80 21163

[51] Int. Cl.⁴ .................. G08B 23/00; G08B 25/00
[52] U.S. Cl. ........................... 340/683; 73/572; 181/125; 340/540; 340/566
[58] Field of Search ............... 340/683, 566, 540, 524; 181/125; 367/124, 127; 376/249; 73/572

[56] References Cited

U.S. PATENT DOCUMENTS

| | | | |
|---|---|---|---|
| 2,535,255 | 12/1950 | Barnes et al. | 367/127 |
| 2,721,315 | 10/1955 | Snyder | 181/125 |
| 3,222,634 | 12/1965 | Foster | 181/125 |
| 3,445,836 | 5/1969 | White et al. | 340/566 |
| 3,471,846 | 10/1969 | Cotter et al. | 340/566 |
| 3,579,220 | 5/1971 | Stevenson, Jr. | 340/566 |
| 4,392,214 | 7/1983 | Marini et al. | 340/683 |

*Primary Examiner*—Glen R. Swann, III
*Attorney, Agent, or Firm*—Pollock, Vande Sande & Priddy

[57] ABSTRACT

Acoustic waves are sensed in contact with or near the plant at at least two points (1, 2, 3, 4) whose position is accurately determined with respect to the monitored region. The order of arrival of the acoustic waves at the sensing points (1, 2, 3, 4) is determined and this order is compared with a predetermined order corresponding to a phenomenon occurring in the monitored region. An alarm is triggered if the order of arrival corresponds to the predetermined order. The apparatus includes an encoding logic (9), a comparator (10) and a monostable circuit (12) triggering the alarm. The invention is particularly applicable to monitoring nuclear reactors in operation.

2 Claims, 9 Drawing Figures

METHOD AND APPARATUS FOR ACOUSTICALLY MONITORING AN INDUSTRIAL PLANT

This application is a continuation-in-part of application Ser. No. 301,848, filed Sept. 14, 1981, now abandoned.

FIELD OF THE INVENTION

The invention concerns a method of acoustically monitoring an industrial plant to detect the formation or development of incidental phenomena which may occur in at least one defined region of this plant, by sensing acoustic waves accompanying these phenomena.

BACKGROUND OF THE INVENTION

In a complex, large industrial plant such as a pressurized water nuclear reactor, unwanted incidental phenomena may occur, such as fracturing, friction between neighboring parts or impact between a structural element of the reactor and a mechanical member such as a bolt, a washer or a valve element which becomes detached from the structure of the reactor and moves at high speed within it. Such a mechanical member detached from the structure of the reactor is carried along by the cooling water of the reactor which circulates at very high speed.

In practice, in plants such as pressurized water nuclear reactors, because of the stresses experienced by parts in service, these being stresses of thermal or mechanical origin, for example, more or less complete local fractures may occur which can develop to the point of a part becoming detached from the structure and being carried along by the flow to become a migrant body in the plant. The effect of stresses is also increased by corrosion.

Also, before the part becomes completely detached from the structure, or where the connection between the part and the structure is being completely destroyed, friction or impact may occur between the part becoming detached and the part of the plant located near it.

In all instances, it is essential to detect the fracture, friction or impact phenomena as rapidly as possible and to monitor their development before they cause significant damage in the plant.

The use has long been proposed of acoustic sensing devices positioned on the structure of the plant or microphones positioned in the atmosphere near the structure in which these destructive phenomena may occur, to sense or record the acoustic waves accompanying the incidental phenomena requiring very rapid detection.

For example, acoustic sensing devices for supplying a signal in response to excitation by acoustic waves have been installed near the regions in which the probability of impact is large or near parts with a considerable probability of fracture.

In a complex industrial plant which is in operation, however, acoustic waves may be produced at various locations in the plant, because, for example, machine members such as pumps or fans are in practically continuous operation.

In the case of nuclear reactors, noise of very varied origin, such as noise accompanying closure of the flap of a valve, the movement of control rods or other movable members can create acoustic signals of the impulse type which are observed at the sensing device terminals and which can be taken for signals resulting from an impact or friction between two parts or from cracks propagated at the moment when a part fractures.

It is very difficult to discriminate effectively between signals due to incidental phenomena and signals due to other causes whose origin can be located in a remote part of the plant.

In particular, currently known apparatuses do not allow a weak acoustic excitation whose source is nearby to be distinguished from a greater excitation created a long way off.

For example, in the case of nuclear reactors, known apparatuses do not allow distinguishing of acoustic waves due to an impact on the bottom of a steam generator and closure of a valve flap a long way from the region in which the sensing device is located. The use of recordings from sensing devices by an electronic monitoring apparatus therefore makes it necessary to take account of the behavior of signals and to analyze them by using an oscilloscope.

In addition, electrical interference may be perceived by the monitoring chain as an acoustic pulse which causes false alarms.

Apparatuses have also been proposed which can be used in the field of non-destructive testing of materials which allow a source of acoustic emissions to be exactly located, for example a fault in the structure of material which emits acoustic waves under the effect of stress.

For this technique, an array of sensing devices is disposed in contact with the structure or material being tested, the time intervals separating the arrival of acoustic waves at the various sensing devices of the array are measured, and these measurements are processed to locate the source of acoustic emissions.

However, such a unit for measuring and processing acoustic signals is very complex, and in the case of an industrial plant, a processing unit of very great capacity, and hence very expensive, would have to be used to obtain accurate location of each source emitting an acoustic signal picked up by the set of sensing devices.

Furthermore, distinguishing various acoustic signals by locating their emission source would also pose problems which would be difficult to solve technically, if very rapid processing and triggering of an alarm is required before the recorded phenomenon has developed to any great extent.

SUMMARY OF THE INVENTION

According to the invention, there is provided a method of acoustically monitoring an industrial plant to detect the formation or development of incidental phenomena which may occur in at least one defined region of this plant, by sensing acoustic waves accompanying these phenomena, this method having to allow very rapid and very easy processing of data from the sensing devices and effective and very simple distinguishing of the sources responsible for acoustic emissions, to determine those located in the region or regions over which monitoring of the plant is exercised.

To obtain this result:
  acoustic waves are sensed in contact with or near the plant, at at least two points whose position is accurately determined with respect to the region in which monitoring is carried out,
  the order of arrival at the sensing point for acoustic waves corresponding to each of the phenomena producing noise in the plant is determined, for at least some of these sensing points, this order of arrival of the waves at the sensing points is compared with a predetermined order of arrival produced at any location in the monitored region, and an alarm is triggered if the order of arrival of the waves at the sensing point corresponds to the predetermined order of arrival.

When the extent of the regions is required to be decreased or when the noise-emitting source is required to be more accurately determined, the monitoring method can be improved.

To achieve this, the sensing point at which the acoustic waves arrive first is determined, the time intervals separating the arrival of the acoustic waves at the sensing points are determined for at least some of the sensing points, and these time intervals are compared with a set of predetermined time intervals defined as a function of the sensing point at which the acoustic waves arrive first and corresponding to the production of an acoustic phenomenon in a defined region of the plant.

BRIEF DESCRIPTION OF THE DRAWINGS

In order that the invention may be more clearly understood, several embodiments of monitoring apparatuses, allowing implementation of the method according to the invention, will now be described with reference to the accompanying drawings, wherein:

FIG. 1a is a diagram showing in greater detail the structure of one of the elements of the embodiment of FIG. 1.

DESCRIPTION OF PREFERRED EMBODIMENTS

Figure 1:
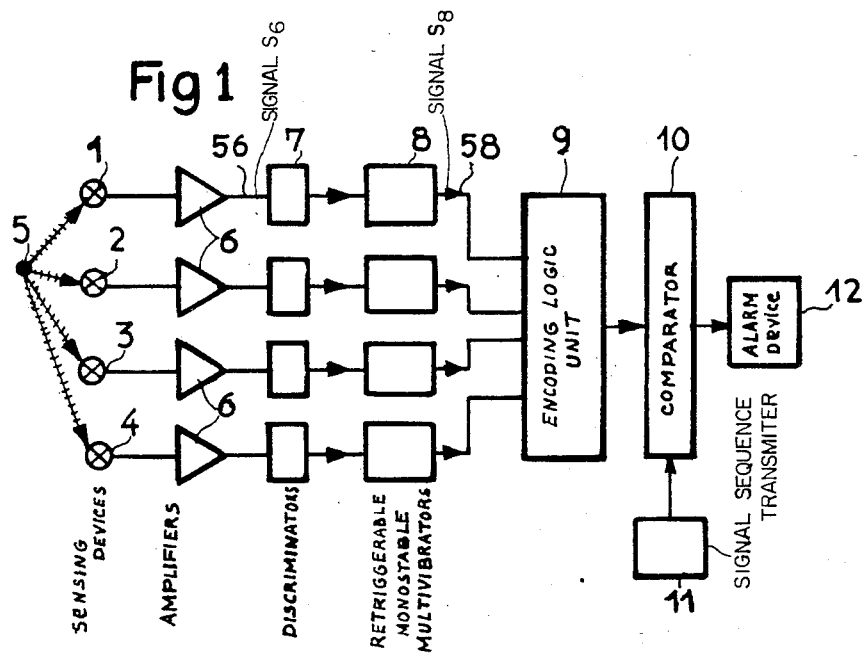
FIG. 1 shows an apparatus according to the invention, allowing the determination of the order of arrival of acoustic waves coming from the same source at a set of four sensing devices.

FIG. 1 shows a source 5 of acoustic emissions emitting waves in all directions inside material constituting the plant in which four sensing devices 1, 2, 3 and 4 are arranged at predetermined locations.

These sensing devices are arranged in a mesh the geometry of which is determined by calculation or experiment so as to optimize the subsequent processing of acoustic waves, and which is disposed partly or wholly in the region to be monitored.

These sensing devices are piezo-electric sensing devices of the differential type and are provided to operate at temperatures of 0° to 350° C. Their resonance frequency is of the order of 200 to 300 kHz.

Figure 2:
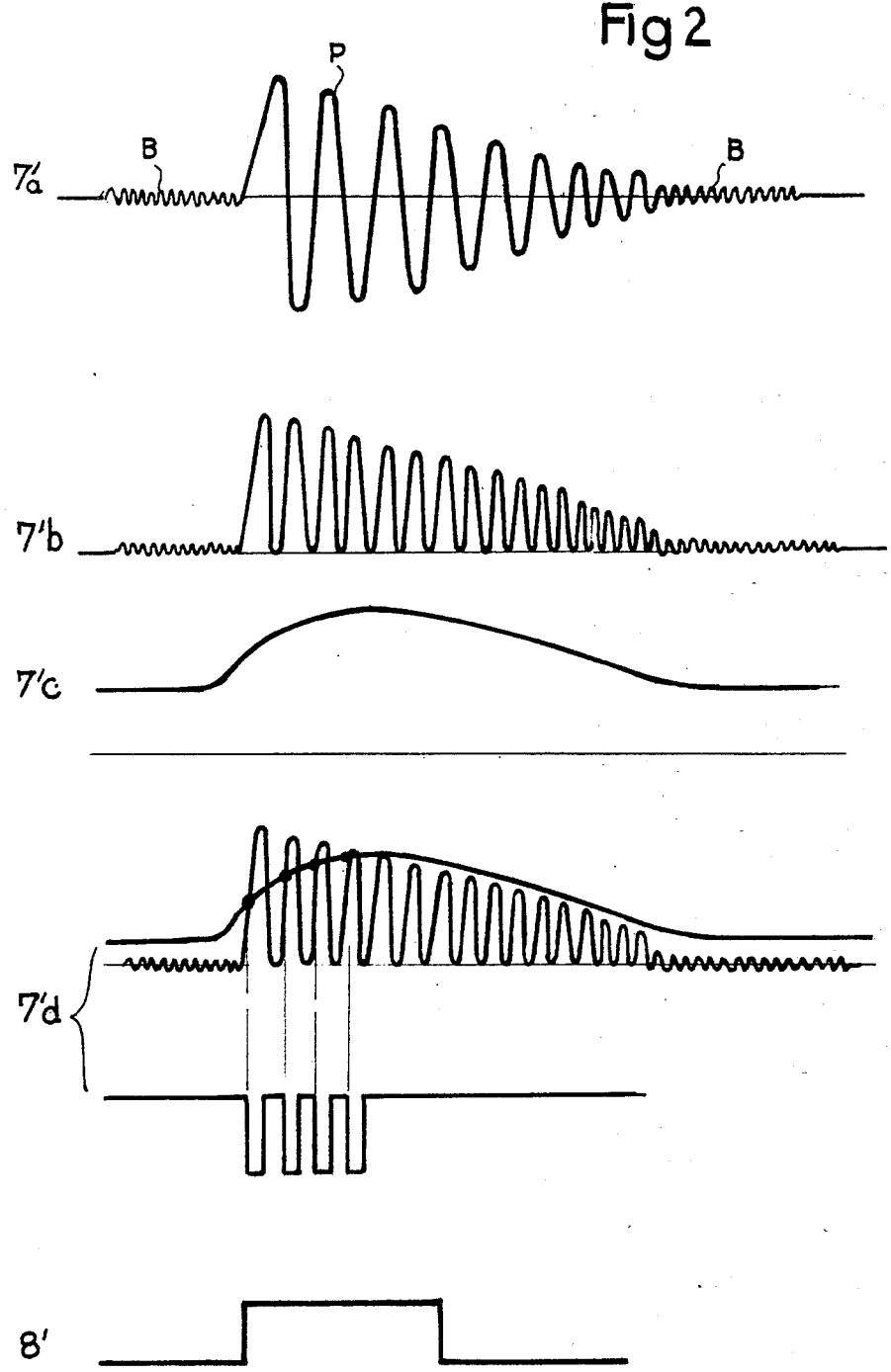
FIG. 2 represents the signals processed by the apparatus of FIG. 1.

The sensing devices 1, 2, 3, 4 convert the acoustic waves received from the source 5 into high-frequency signals repesented in FIG. 2. These high-frequency signals are processed by a chain comprising, for each of the sensing devices, an amplifier 6, a signal discriminator 7 which will be described in detail with reference to FIG. 1a and a retriggerable monostable multivibrator 8. The amplifier 6 is installed at a distance of less than 10 meters from its sensing device. Its pass-band ranges from 30 kHz to 2 MHz and its gain is fixed and adjusted locally to 20, 40 or 60 dB.

As visible in FIG. 1a, the signal discriminator 7 comprises several components connected as indicated in the figure. The component 7a is a high pass filter which comprises four adjustable frequency ranges (50–100–20 0–400 kHz).

The component 7b is a rectifying module.

The component 7c is a module for forming an envelope signal.

The component 7d is a signal comparator and emitter module.

The functions of these components are specified below, with reference to FIG. 2.

In FIG. 2, are shown the signals obtained at the output of the component 7a, 7b, 7c, 7d and 8. These signals are each denoted by the reference numerals of the corresponding component with addition of the sign '.

The signal 7'a corresponds to the high-frequency signal transmitted by the sensing device (1, 2, 3 or 4), amplified by the amplifier 6 and filtered by the high pass filter 7a. This signal 7'a comprises a background noise B connected with the operation of the industrial installation. The amplitude of the background noise is hence not constant but depends on the operating phases of the installation. When an accidental phenomenon occurs, a disturbance P appears in the signal 7'a. The amplitude of the signal manifesting the disturbance P is much greater than the amplitude of the background noise signal B.

The signal 7'a is subjected to full wave rectification in the rectifying module 7b, to give the signal 7'b.

The module 7c develops the envelope signal 7'c which is obtained by the addition of a signal of fixed value adjustable to the signal 7'b. For the rectified signal corresponding to the background noise B, the envelope signal 7'c develops parallel with the rectified signal B, but with a slight delay arising from its mode of formation.

When a disturbance P appears, the envelope signal can no longer follow the sudden variations in amplitude of the rectified signal. The first alternations of the signal 7'b hence exceed the envelope curve in amplitude.

The component 7'd of the discriminator 7 enables the points of intersection between the signal 7'd and the envelope signal 7'c to be detected, by comparison of the two signals. The component 7d uses the envelope signal 7'c as giving threshold values to trigger all or nothing signals of constant amplitude 7'd.

The disturbance P associated with the appearance of an accidental phenomenon is manifested therefore at the output of the component 7d by a sequence of pulses.

In the module 8 which is a retriggerable monostable circuit, the first pulse of the signal 7'd triggers an all or nothing signal 8' of predetermined constant duration.

The start of this signal 8' corresponds to the instant Ti when the acoustic waves accompanying an incident arrive at the corresponding sensing device.

Only the order of arrival (and possibly the time separations Δt separating the reception of the signals at each of the sensing devices) are then taken into account and obtained from the signals 8'.

The signals 7'b, 7'c or 7'd can be collected at test points T1, T2 and T3, respectively, and displayed on a cathode screen or a rapid recording panel. The operators can thus easily carry out adjustments on the displayed signals.

The signals 8' coming from the retriggerable monostable multi-vibrators corresponding to the sensing devices 1, 2, 3 and 4 arrive at a module 9 which comprises a coding logic for the attribution of a code to each of the signals 8' according to its order of arrival in the module 9 and its emission line, each emission line corresponding to one of the sensing devices 1, 2, 3 and 4. The data relating to the order of the signals are hence obtained in digital form in the module 9. A module 11 enables an operator to record a predetermined arrival sequence of the signals, in digital form and to transmit this sequence to a comparison module 10. This sequence manifests, when it is detected, the presence of an accidental phenomenon in the monitored area of the plant.

The comparator module 10 enables comparison of the order of the signals translated into digital form by the coding module 9 with the predetermined sequence transmitted in digital form by the module 11.

In the case of identity between the data received by the comparator 10, the latter acts on a monostable circuit 12 which emits in response an all or nothing signal. This signal is an indication of an accidental phenomenon in the monitored zone of the installation and enables an alarm to be triggered.

The modules 7, 8, 9, 10, 11 and 12 are constituted by logic components of the "CMOS" and "TTL" type marketed by companies such as Texas Instruments, National Semiconductors, Harris and Motorola.

Figure 3:
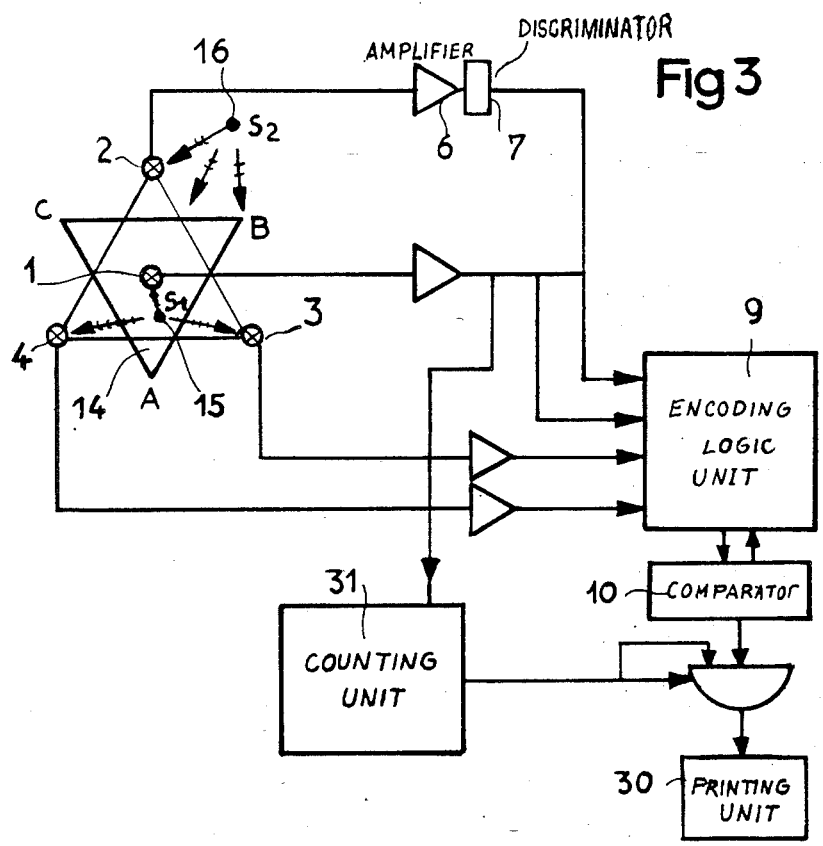
FIG. 3 shows diagrammatically an apparatus with four sensing device used for monitoring an industrial plant.

FIG. 3 shows a way of applying an apparatus for determining the sequence of arrival of signals at a set of sensing devices arranged in a plant in which a region with a particular position and shape is required to be monitored.

The region 14 to be monitored is shaped like an equilateral triangle ABC and the acoustic sensing devices 1, 2, 3 and 4 are arranged with the sensing device 1 at the center of the triangle ABC and with the sensing devices 2, 3 and 4 symmetrical with the sensing device 1 with respect to the sides BC, AB and AC, respectively, of the equilateral triangle ABC constituting the monitoring region 14.

The acoustic signals received by the sensing devices and converted to high-frequency signals are processed by amplifiers 6 and discriminators 7 to convert the signals as described hereinbefore.

The signals are then processed in a unit 9 for determining the order of arrival and a comparator 10 allows determination of whether or not there is identity between the order of arrival at the sensing devices and a preselected order of arrival.

If there is identity, an authorization signal is transmitted, and this signal triggers an alarm or printing of a piece of information at a printing unit 30.

In the case of a region 14 like that represented in FIG. 3, it is sufficient to determine the sensing device which first receives the acoustic emission. In practice, if there is assumed to be a source 15 of acoustic emissions disposed inside the region 14 and a region 16 of acoustic emissions disposed outside, it is quite clear that the source 15 is nearer the sensing device 1 than the other sensing devices 2, 3 and 4 and that conversely the source 16 is nearer at least one of the sensing devices 2, 3 and 4 than the sensing device 1.

All that has to be determined, therefore, to discover whether the source of acoustic emissions is disposed in the region 14 or outside this region, is which sensing device first receives the acoustic emission. In practice, the acoustic waves move at constant speed in the material constituting the plant the region 14 of which is monitored, and the travelling time of these acoustic waves is dependent only on the distance from the source of acoustic emissions to the sensing device which receives it.

If the sensing device first receiving the acoustic emission is the sensing device 1, the source of acoustic emissions is hence definitely in the region 14 and, conversely, if the sensing device first receiving the acoustic emission is another sensing device (2, 3 or 4), the source 16 of acoustic emissions is, also definitely, outside the region 14.

The single comparison made at the comparator 10 is hence a comparison between the code of the signal coming from the sensing device which first received the acoustic emission and the predetermined code corresponding to an acoustic emission first received by the sensing device 1.

If there is identity between these two codes, the authorization signal is transmitted and in addition processing is initiated in a unit 31, on the signal emitted by the sensing device 1, to determine, for example, the energy of the acoustic source located in the region 14 being monitored.

This processing can be constituted, for example, by counting of the number of pulses in the signal amplified and converted by the discriminator 7. This signal is similar to signal 7'd shown in FIG. 2.

Figure 4:
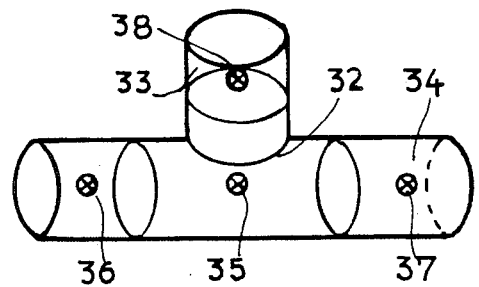
FIG. 4 represents the arrangement of the sensing devices of an apparatus for monitoring the weld region of a tapping from a pipe system.

FIG. 4 shows another application of the method according to the invention, this being used for monitoring a weld region 32 at the junction between a tapping 33 and a pipe system 34.

Four sensing devices are used, the first three sensing devices 35, 36 and 37 being arranged respectively on the axis of the pipe system 34, and the fourth on the axis of the tapping 33.

The sensing device 35 is disposed near the weld region 32, while the sensing devices 36 and 37 are arranged symmetrically on either side of the sensing device 35 inside the pipe system 34.

An arrangement is selected in which the sensing device 35 is much nearer the weld region than the other sensing devices.

To sense an acoustic emission originating in the weld region, due, for example, to the onset of fracture in this weld region, all that has to be determined is identity between a selected event, i.e., the arrival of the acoustic signal first at the sensing device 35, and that actually observed.

A piece of equipment of the type represented in FIG. 3, which uses determination of the sensing device first receiving the acoustic emission as its sole distinguishing element, can therefore be used.

Figure 5:
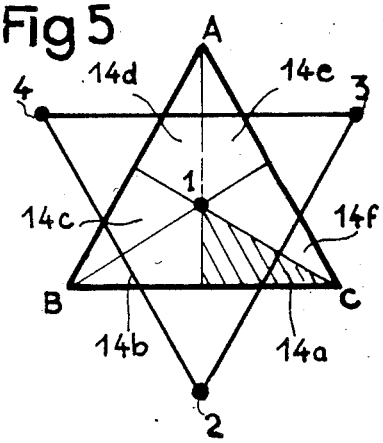
FIG. 5 represents the spatial distribution of the regions which can be monitored by means of an apparatus with four sensing devices.

An arrangement of sensing devices identical to that represented in FIG. 3 is shown is FIG. 5, and inside the region 14, regions 14a, 14b, 14c, 14d, 14e and 14f, the boundaries of which are the mid-perpendiculars of the triangle ABC passing through the center of the triangle in which the sensing device 1 is found, have also been delimited.

If the region 14a bounded by part of the side BC of the triangle ABC and by two mid-perpendiculars of the triangle formed by the sensing device is considered, it will be seen that any point in this region 14a is nearer the sensing device 1 than the other sensing devices and that any point in this region 14a is nearer the sensing device 2 than the sensing device 3.

Therefore, if the signals arrive at the sensing devices 1, 2, 3, 4 in such a way that these acoustic signals first arrive at the sensing device 1, then at the sensing device 2 and lastly at the sensing device 3, the point of emission of these signals is disposed inside the region 14a.

A more accurate delimitation of regions to identify the point of emission of the acoustic waves is therefore possible, by considering the order of arrival after the first sensing device.

Figure 6:
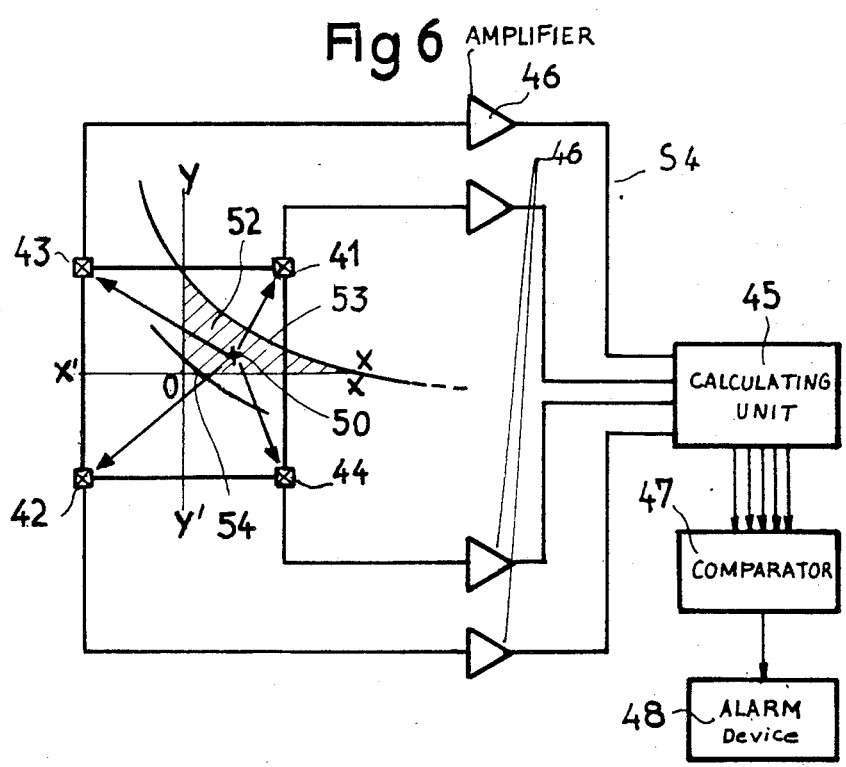
FIG. 6 represents an apparatus with four sensing devices used for monitoring a delimited region of an industrial plant.

With reference to FIG. 6, it can be seen that it is possible to accurately delimit regions on the surface where the sensing devices occur by using measurements of the time intervals separating the arrival of acoustic waves at a set of sensing devices arranged in an array on the surface of the plant to be monitored.

FIG. 6 shows four acoustic sensing devices 41, 42, 43 and 44 arranged in a square array on the surface; which is metal, for example, of a plant to be monitored, such as the curved bottom of a nuclear reactor vessel or of a steam generator associated with a nuclear reactor.

The signals coming from the acoustic sensing devices 41, 42, 43, 44 are processed by amplifiers 46 and then by a calculating unit 45.

The calculating unit comprises a processing unit for the signals S46 coming from the amplifiers 46. This processing unit is similar to the device described with reference to FIGS. 1 and 1a, and enables in particular the determination of the sensing device where the acoustic waves connected with an accidental phenomenon have arrived first.

The calculating unit 45 includes also a module for the development of all or nothing signals of which the initial moment corresponds to the arrival of the acoustic waves at the first sensing device and the final moment to the arrival of the acoustic waves at the succeeding sensing devices, respectively. This module is constituted by commercial logic components, like the processing unit described with reference to FIGS. 1 and 1a.

Figure 7:
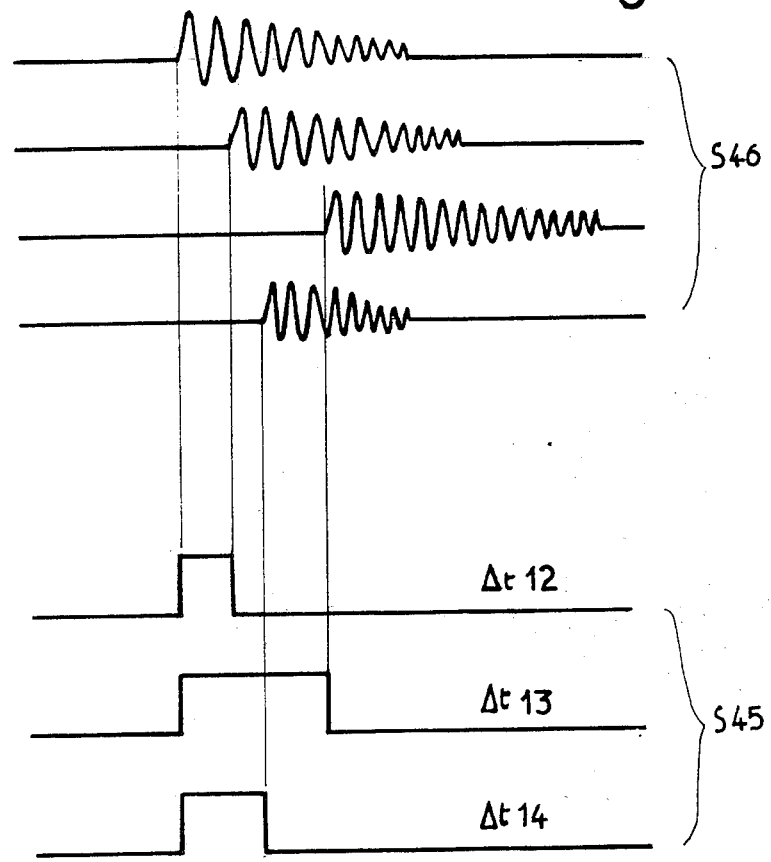
FIG. 7 represents the signals processed by the apparatus of FIG. 6.

FIG. 7 shows, in its upper portion, the signals S46 emitted at the output of the amplifiers 46, of which the order at the sensing devices is 1-2-3-4.

In the lower portion, there are shown the all or nothing signals S45 at the output of unit 45 of respective durations of $\Delta t\, 1,2$, $\Delta t\, 1,3$ and $\Delta t\, 1,4$.

As FIG. 7 shows, the signals represented relate to an acoustic emission from a point located inside the first quadrant bounded by the axes OX and OY represented in FIG. 6. In practice, the acoustic waves arrive first at the sensing device 41 before arriving at the sensing devices 42, 43 and 44 for all the points located in this first quadrant.

For example, in the case of an emitting point 50 disposed in the first quadrant containing the first sensing device 41, the unit for determining the order of arrival of acoustic waves at the sensing devices identifies the sensing device 41 as the first sensing device receiving the acoustic wave, and transmits this piece of information to the calculating unit which determines the $\Delta T$'s separating the arrival of waves at the sensing device 41 from the arrival of waves at the sensing devices 42, 43 and 44, respectively.

A monitoring region 52 has also been determined inside the first quadrant OX-OY bounded by the axes OX-OY and by two hyperbolic branch portions 53 and 54 whose foci are the points on the surface where the sensing devices 41 and 42 are disposed.

The difference in the distances separating these points of the sensing devices 41 and 42 are constant for each of the points of these hyperbolic branches 53 and 54.

For an acoustic emission to originate from a point in the region 52, for example the point 50, the first sensing device reached by the acoustic wave must therefore be the sensing device 41, and in addition the value $\Delta T1_2$, which is the time interval separating the arrival of waves at the sensing, device 2 from the arrival of waves at sensing device 1 must be between two predetermined fixed values which correspond to points located on the hyperbolic branches 53 on the one hand and 54 on the other.

When the unit associated with the calculating unit 45 has determined that the sensing device 41 was the first to receive the acoustic waves, the spatial discrimination logic unit 47, receives a signal representing $\Delta T1_2$ as a consequence and this signal is compared by the discrimination logic 47 with the two predetermined values corresponding to the limits of the region 52.

Figure 8:
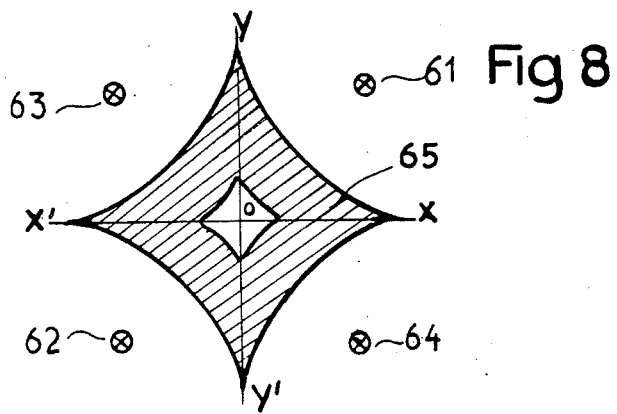
FIG. 8 represents the group of regions of a plant which can be monitored by an apparatus like that represented in FIG. 6.

FIG. 8 shows part of a nuclear reactor vessel bottom on which four sensing devices 61, 62, 63 and 64 have been arranged in a square array and on which a complex region 65 has been marked out, in which monitoring of incidental phenomena such as impacts against the wall is required to be carried out.

The region 65 is constituted by four region portions, such as the region 52 represented in FIG. 6 bounded by the half-axes OX, OY, $OX^{1\ l\ and\ OY_1}$, and hyperbolic branch portions whose foci are respectively identical with the acoustic wave sensing points 61 and 62 on the one hand and 63 and 64 on the other.

In the case of acoustic emissions transmitted by the wall of the nuclear reactor vessel, a measuring and discriminating apparatus of the type represented in FIG. 6 allows the quadrant in which the acoustic emission source is to be found to be determined and the values of $\Delta T1_2$ or $\Delta T_2$ to be supplied to the discrimination logic 47 which allows determination of whether these values come between two assigned values corresponding to positions of the acoustic emission source on the hyperbolic branches bounding the region 65 in the quadrant containing the sensing device 61 and in the quadrant containing the sensing device 62.

Similarly, in the case of the acoustic emission having been first received by the sensing device 63 or by the sensing device 64, the processing unit 45 allows the values of $\Delta T3_4$ or $\Delta T4_3$ to be calculated, the discrimination logic 47 allowing these values to be compared with the predetermined and prerecorded values corresponding to the positions of acoustic emission sources on the hyperbolic branches bounding the region 65 in the quadrant containing the sensing device 63 and in the quadrant containing the sensing device 64.

The principal advantage of the method according to the invention is that it allows very easy and very rapid spatial discrimination of the origin of the emission of acoustic waves, either by using solely the order of arrival of acoustic waves at the sensing devices arranged in a particular way with respect to the regions to be monitored, or by using both the order of arrival of acoustic waves at the sensing devices and the value of the time intervals separating the arrival of these acoustic waves at at least some of these sensing devices.

The invention is obviously not limited to the embodiments described.

Thus, use of any number of sensing devices is conceivable, and theoretically a spatial discrimination can be achieved with two sensing devices, although this is limited to determining in what half-plane or half-space the source of acoustic emission is to be found.

The limits of the region to be monitored can of course be more precisely defined by increasing the number of sensing devices.

When the region to be monitored is small, it is clearly advantageous to dispose one sensing device in its immediate vicinity and other sensing devices at greater distances from the region. In particular, if sensing devices are arranged in this way about the sensing device located near the region to be monitored in very many directions in space, discrimination can be carried out very effectively.

The invention has been largely described in the context of its use in the case of nuclear reactors, but it is also possible to envisage it being used in any industrial plant, particularly in a complex, large industrial plant such as a refinery or a petrochemical plant.

We claim:

1. Apparatus for acoustically monitoring an industrial plant in a defined monitoring region of which incidental phenomena accompanied by acoustic waves may occur, the monitoring region being in the shape of an equilateral triangle and the apparatus comprising
    (a) a set of four sensing devices arranged at the center of a first equilateral triangle constituting said monitoring region and at locations symmetrical with said center with respect to the sides of said first equilateral triangle, respectively, said sensing devices thus being arranged at the vertices and at the center of a second equilateral triangle having a common center with said first equilateral triangle; and
    (b) for each of said sensing devices, an amplifier and a discriminator of signals emitted by said sensing device in response to the reception of acoustic waves, and a retriggerable monostable multivibrator following said discriminator and producing from the signal emitted and converted by said sensing device a signal of fixed amplitude and duration the initial instant of which corresponds to the exact instant of arrival of the signals at each of said sensing devices;
    (c) a logic unit for determining the order of arrival of acoustic waves at said sensing devices by discrimination of the signals from said multivibrators;
    (d) a comparator of said order of arrival with a predetermined coded order of arrival and an associated means for emitting a signal in the case of an identity of said orders of arrival; and
    (e) alarm means which are triggered when said signal is emitted in the case of identity.

2. Apparatus according to claim 1, comprising means for counting the number of pulses of the signal from the sensing device which first received the acoustic wave, in response to the signal emitted in the case of identity.

* * * * *